(12) United States Patent
Yoshida et al.

(10) Patent No.: US 8,765,109 B2
(45) Date of Patent: *Jul. 1, 2014

(54) COSMETICS HAVING EXCELLENT USABILITY AND STABILITY AND A METHOD FOR MAKING THE SAME

(75) Inventors: Mari Yoshida, Narita (JP); Yuki Kokeguchi, Narita (JP)

(73) Assignee: Kokyu Alcohol Kogyo Co., Ltd., Narita-shi (JP)

( * ) Notice: Subject to any disclaimer, the term of this patent is extended or adjusted under 35 U.S.C. 154(b) by 372 days.

This patent is subject to a terminal disclaimer.

(21) Appl. No.: 12/344,342

(22) Filed: Dec. 26, 2008

(65) Prior Publication Data

US 2009/0280077 A1 Nov. 12, 2009

Related U.S. Application Data

(60) Provisional application No. 61/052,311, filed on May 12, 2008.

(30) Foreign Application Priority Data

May 14, 2008 (JP) ................................. 2008-127290

(51) Int. Cl.
- *A61K 8/88* (2006.01)
- *A61K 8/06* (2006.01)
- *A61K 8/44* (2006.01)
- *A61Q 1/02* (2006.01)

(52) U.S. Cl.
CPC ............ *A61Q 1/02* (2013.01); *A61K 2800/262* (2013.01); *A61K 8/88* (2013.01); *A61K 8/442* (2013.01)
USPC ........................... 424/78.03; 424/63; 424/401

(58) Field of Classification Search
None
See application file for complete search history.

(56) References Cited

U.S. PATENT DOCUMENTS

| | | |
|---|---|---|
| 2002/0159961 A1 | 10/2002 | Yamato et al. |
| 2004/0223987 A1 * | 11/2004 | Ferrari .......................... 424/401 |
| 2005/0191327 A1 * | 9/2005 | Yu et al. ......................... 424/401 |
| 2006/0078581 A1 | 4/2006 | Yamato |
| 2006/0204460 A1 | 9/2006 | Takeda |
| 2006/0280763 A1 * | 12/2006 | Yoshida et al. ............... 424/401 |
| 2007/0243151 A1 | 10/2007 | Healy |

FOREIGN PATENT DOCUMENTS

| | | |
|---|---|---|
| JP | 07-098731 B2 | 4/1989 |
| JP | 2002-316971 A | 10/2002 |
| JP | 2004-517856 A | 6/2004 |
| JP | 2004536083 A | 12/2004 |
| JP | 2005298635 | 10/2005 |
| JP | 2005533105 A | 11/2005 |
| JP | 2007246453 A | 9/2007 |
| JP | 2008019200 | 1/2008 |
| JP | 2008031170 A | 2/2008 |
| JP | 2008050305 A | 3/2008 |
| WO | WO2004006877 | 1/2004 |
| WO | WO 2006-013489 A1 | 12/2006 |

OTHER PUBLICATIONS

Keitaro Saito et al., Characteristics of Novel Oil Gelling Agents Derived From Amino Acid and Their Applications to Cosmetics, Frangrance Journal, Jul. 2007 pp. 60-65.*
U.S. Appl. No. 12/332,331, filed Dec. 2008, Yoshida et al.*
European Patent Office, Supplementary European Search Report, Application Ser. No. EP 08 87 4283, Aug. 11, 2011.
Keitaro Saito et al., "Characteristics of Novel Oil Gelling Agents Derived . . . ", Fragrance Journal, Jul. 15, 2007, pp. 60-65, 35(7), Japan.
English translation of ISR for PCT/JP2008/073787, mailed Mar. 10, 2009.
ISR for PCT/JP2008/073787, mailed Mar. 10, 2009.

* cited by examiner

*Primary Examiner* — H. Sarah Park
(74) *Attorney, Agent, or Firm* — The Harris Firm

(57) ABSTRACT

A cosmetic comprising an amino acid oil gelling agent, a polyamide resin and a monoester, wherein the amino acid oil gelling agent is one or more selected from dibutyl ethylhexanoyl glutamide and dibutyl lauroyl glutamide, and wherein said monoester is one or more selected from a monoester having a $C_9$ to $C_{24}$ linear chain or branched chain fatty acid moiety and/or a $C_9$ to $C_{24}$ linear chain or branched chain alcohol moiety, and said monoester is 20-80 mass % of the cosmetic. Cosmetic products, and methods for making and preparing cosmetics.

7 Claims, No Drawings

COSMETICS HAVING EXCELLENT USABILITY AND STABILITY AND A METHOD FOR MAKING THE SAME

This application is based upon and claims priority under 35 USC §119(e) to U.S. provisional application Ser. No. 61/052,311, filed May 12, 2008, and is based upon and claims priority under 35 USC § 119(b) to Japanese application Ser. No. JP 2008-127290, filed May 14, 2008, both of which are herein incorporated by reference in their entireties.

TECHNICAL FIELD

The present invention relates to cosmetics having excellent usability and storage stability and a method for making the same. In more detail, the present invention relates to cosmetics having excellent usability and storage stability comprising an amino acid oil gelling agent, a polyamide resin, and a specific monoester, and a method for making the same, etc.

BACKGROUND ART

As to performances of cosmetic products, an importance as to not only makeup effect, but also usability is increasing, whereas such usability is influenced by the kind of a cosmetic used. For example, in order to improve usability of the cosmetic product, it has been reported that natural polysaccharides or cationized natural polysaccharides are used (Patent Document 1).

Further, it has also been reported that dibutyl ethylhexanoyl glutamide and dibutyl lauroyl glutamide that are oil gelling agents are used in cosmetics for the purpose of a stable foam, etc. (Patent Documents 2 to 5).

Moreover, Patent Document 6 discloses a gel-like composition, wherein a specified amino acid derivative oil gelling agent is blended in order to uniformly mix the oil gelling agent into an oily base under the condition of a relatively low temperature.

Further, as to an oil gelling agent used for a cosmetic for the purpose of moisturizing effect, dextrin fatty acid esters, polysaccharide fatty acid esters, clay minerals modified with organic compounds, and 12-hydroxystearic acid, etc., are known (Patent Document 7).

Moreover, Patent Documents 8 and 9 disclose a cosmetic blended with a polyamide resin for the purpose of improving gel strength and usability, etc.

Also, Patent Document 10 discloses a cosmetic product composition to which dibutyl lauroyl glutamide, an amide-terminated polyamide resin and an ester-terminated polyamide resin is blended for the purpose of improving shape storage stability and mechanical strength.

However, no above-described literature discloses a cosmetic product comprising three ingredients of an amino acid oil gelling agent, a polyamide resin and a specific monoester according to the present invention at the same time, and the oil gelling agent, the polyamide resin and the monoester alone do not improve usability and storage stability of a cosmetic in combination.

As above, at present, there is no cosmetic product comprising three ingredients of an amino acid oil gelling agent, a polyamide resin and a specific monoester at the same time, and provided with sufficient storage stability together with excellent usability, and no cosmetic capable of manufacturing such a cosmetic product. That is, it is an actual state that a cosmetic product having sense of non-tackiness etc. and excellent usability has poor storage stability.

Therefore, developments of a technology and a product for realizing a cosmetic having more excellent usability and storage stability in combination are required strongly.

[Patent document 1] JP, A, 2008-50305
[Patent document 2] JP, A, 2008-31170
[Patent document 3] JP, A, 2005-533105
[Patent document 4] JP, A, 2004-536083
[Patent document 5] JP, A, 2008-19200
[Patent document 6] JP, A, 2005-298635
[Patent document 7] JP, A, 2007-246453
[Patent document 8] U.S. Patent Publication No. 2006/0280763
[Patent document 9] JP, B, 7-98731
[Patent Document 10] U.S. Patent Publication No. 2005/0191327

DISCLOSURE OF INVENTION

Problems to be Solved by the Invention

It is an object of the present invention to provide a cosmetic having more excellent usability and sufficient storage stability in combination and a method for making the same, etc.

Means for Solving the Problems

In order to solve the above-described problems, the present inventors have found that usability and storage stability of a cosmetic product that is a shaped product are improved as compared to a cosmetic that comprises each of the ingredient alone by using an amino acid oil gelling agent, a polyamide resin and a specific monoester in combination, and as a result of a further intensive research, completed the present invention.

That is, the present invention relates to a cosmetic comprising an amino acid oil gelling agent, a polyamide resin and a monoester, wherein said monoester is one or more selected from a monoester having a $C_9$ to $C_{24}$ linear chain or branched chain fatty acid residue and/or a $C_9$ to $C_{24}$ linear chain or branched chain alcohol residue.

Also, the present invention relates to the above-described cosmetic, wherein the amino acid oil gelling agent is one or more amino acid derivatives represented by the following general formula (1)

[Chem. 1]

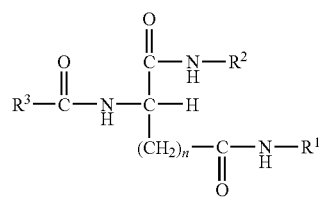

(wherein, $R^1$ and $R^2$ represent a $C_1$ to $C_{10}$ linear chain or branched chain alkyl group which may be the same or different from each other, $R^3$ represents a $C_1$ to $C_{26}$ linear chain or branched chain alkyl group, n represents an integer of 1 or 2.)

Further, the present invention relates to the cosmetic, wherein the amino acid oil gelling agent is one or more comprising at least dibutyl lauroyl glutamide.

Also, the present invention relates to the cosmetic, wherein the polyamide resin is one or more selected from an amide-terminated polyamide resin and an ester-terminated polyamide resin represented by the following general formula (2)

[Chem. 2]

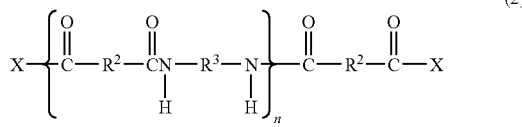

(2)

(wherein, X represents —N(R$^1$)$_2$ group or —OR$^1$ group, wherein R$^1$ represents a C$_8$ to C$_{22}$ linear chain or branched chain alkyl group which may be the same or different from each other, R$^2$ represents a dimer acid residue, R$^3$ represents an ethylenediamine residue, n represents an integer from 2 to 4.)

Further, the present invention relates to the above-described cosmetic, wherein the monoester is one or more selected from the group consisting of isononanoate ester, 2-ethylhexanoate ester, myristate ester, isostearate ester, lactate ester, hydroxystearate ester, oleate ester, neopentanoate ester, palmitate ester, laurate ester, stearate ester, neodecanoate ester and nonanoate ester.

Also, the present invention relates to a cosmetic product comprising any of the above-described cosmetic.

Further, the present invention relates to the above-described cosmetic product, selected from the group consisting of an antiperspirant, a cream, a lip gloss, an eye shadow, a mascara, a lip stick, a hair gel, a hair wax, a hair stick, a hair cream, a sun protection product, a foundation and an eye color.

Also, the present invention relates to a method for making any of the cosmetic described above.

Further, the present invention relates to a method for increasing usability and storage stability of a cosmetic, wherein the method comprises the step of mixing one or more amino acid oil gelling agents, one or more polyamide resins, and one or more monoesters selected from the monoesters having a C$_9$ to C$_{24}$ linear chain or branched chain fatty acid residue and/or a C$_9$ to C$_{24}$ linear chain or branched chain alcohol residue.

As functions generally required for oil gelling agents used for a cosmetic, (1) functions relating to storage stability, (2) functions relating to sensuality, and (3) functions relating to vision etc. against the product is required, whereas as oil gelling agents satisfying each of the above-described functions (1) to (3), amino acid oil gelling agents such as dibutyl lauroyl glutamide are mentioned, all of which include an amino acid residue.

Amino acid oil gelling agents such as dibutyl lauroyl glutamide, etc. are oil gelling agents having excellent properties such as, as described below,
(a) gelling of oil agents, stabilizing of emulsified system (functions relating to storage stability),
(b) improving of feeling and adjusting of thread-forming property when blended into a cosmetic (functions relating to sensuality),
(c) easily obtaining a cosmetic with high transparency (functions relating to vision).
However, even these amino acid oil gelling agents, single amino acid oil gelling agents alone do not have an effect that usability and storage stability of the cosmetic are improved in combination.

Also, the polyamide resin has the effect of cosmetic persistence, and at the same time has properties similar to those of waxes or cera, so that it is known as the ingredient that facilitates formation of a cosmetic, and is possibly blended in a large amount. However, a polyamide resin alone does not have the effect that usability and storage stability of a cosmetic is improved in combination.

Further, it is known that a monoester has the aspect of a liquid oil, and has an effect of adjusting hardness of the shaped product properly, and at the same time increasing solubility of various formulating ingredients at the time of preparation. However, a monoester alone does not have the effect that usability and storage stability of a cosmetic is improved in combination.

On the contrary, the present invention has been made based on the effect of increasing usability (for example, ease of coating, sense of non-tackiness, adhesive property) and storage stability (for example, not separating and sweating for a long time) of a cosmetic product that is a shaped product in combination by comprising three ingredients of an amino acid oil gelling agent, a polyamide resin and a specific monoester at the same time by a synergistic effect of three ingredients.

The mechanism is not always clear that, in the cosmetic of the present invention, usability and storage stability of a cosmetic product that is a shaped product are increased in combination as compared to the cosmetic comprising each of the ingredient alone by using an amino acid oil gelling agent, a polyamide resin and a specific monoester in combination.

For example, in stick formulation, in the cosmetic using an amino acid oil gelling agent alone, though shape retention property of the shaped product is good, there is a tendency of increasing brittleness (mealy texture) and a problem as to flexibility occurs. On the other hand, in the cosmetic using a polyamide resin alone, though flexibility of the shaped product is increased, there is a tendency of increasing soft gummy-like softness (limp and elastic texture) and a problem as to shape retention property occurs. Therefore, it is considered that, by making a cosmetic blending both ingredients at the same time, shape retention property and flexibility of the shaped product is adjusted in a good balance, and usability such as spreadability and adhesive property is improved.

Also, it is considered that, by using in combination an amino acid oil gelling agent and a polyamide resin that are considered to have high compatibility from the point of molecule structure, dispersion property of an amino acid oil gelling agent is increased to form more uniform and dense crosslinking structure, and oily liquid ingredients are stably retained in the crosslinking structure thereof, thereby separation and sweating of the shaped product is prevented effectively.

Further, it is considered that, by blending a specific monoester having high compatibility with an amino acid oil gelling agent and a polyamide resin, the moderate hardness of the shaped product is more optimized, thereby usability such as spreadability, adhesive property, etc. is more improved, and at the same time the compatibility of the oily liquid ingredient comprising a monoester is improved and thereby sweating etc. is prevented more effectively, thereby storage stability is more improved.

Effects of the Invention

The cosmetic of the present invention has the effect that it has excellent usability and sufficient storage stability in combination as compared to the prior cosmetic. Among the cosmetic of the present invention, one or more cosmetics in which the amino acid oil gelling agent comprises at least dibutyl lauroyl glutamide have more excellent usability and storage stability, and in particular, the cosmetic in which the amino acid oil gelling agent is one or more comprising at least dibutyl lauroyl glutamide, and the monoester is one or more selected from the group consisting of isononanoate esters etc. has even more excellent usability and storage stability.

Therefore, the cosmetic of the present invention can be used for wide application of cosmetic products such as an antiperspirant, a cream, a lip gloss, an eye shadow, a mascara, a lip stick, a hair gel, a hair wax, a hair stick, a hair cream, a sun protection product, a foundation, an eye color, and the cosmetic product containing the cosmetic of the present invention is expected to have an effect that usability is excellent, etc.

BEST MODE FOR CARRYING OUT THE INVENTION

In the present specification, "cosmetic product" is not limited specifically, and means various products used for makeup.

Further, in the present invention, "cosmetic" is not limited specifically, and includes various ingredients used for manufacturing of cosmetic products.

Oil gelling agent is an ingredient used for maintaining the product form of the cosmetic stably, and adjusting usebility. The oil gelling agent used in the present invention is an amino acid derivative containing amino acid residue, and preferably, an amino acid oil gelling agent represented by the following general formula (1)

[Chem. 3]

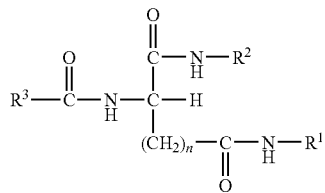

(1)

(wherein, $R^1$ and $R^2$ represent a $C_1$ to $C_{10}$ linear chain or branched chain alkyl group which may be the same or different from each other, $R^3$ represents a $C_1$ to $C_{26}$ linear chain or branched chain alkyl group, n represents an integer of 1 or 2.). In the above general formula (1), $R^1$ and $R^2$ is more preferably a $C_1$ to $C_8$ linear chain or branched chain alkyl group, further preferably a $C_1$ to $C_6$ linear chain or branched chain alkyl group. Also, $R^3$ is, more preferably, a $C_1$ to $C_{20}$ linear chain or branched chain alkyl group, further preferably a $C_1$ to $C_{14}$ linear chain or branched chain alkyl group. It is more preferable to use two or more of these amino acid oil gelling agents in combination.

Here as mentioned above, as to the amino acid oil gelling agent, from the viewpoint of (a) gelling of oil agents, stabilizing of emulsified system (functions relating to storage stability), (b) improving of feeling and adjusting of thread-forming property when blended into a cosmetic (functions relating to sensuality), and (c) easily obtaining a cosmetic with high transparency (functions relating to vision), etc., dibutyl lauroyl glutamide and dibutyl ethylhexanoyl glutamide, etc. are more preferred, dibutyl lauroyl glutamide being particularly preferred. As a specific product name, GP-1 as dibutyl lauroyl glutamide and EB-21 as dibutyl ethylhexanoyl glutamide (both manufactured by AJINOMOTO CO., INC.) etc. are mentioned.

It is more preferable to use two or more of these amino acid oil gelling agents in combination.

The content of the above-described one or more amino acid oil gelling agents used in the present invention is preferably about 0.01 to 15 mass %, more preferably 0.05 to 10 mass %, even more preferably 0.1 to 5 mass %, of the entire cosmetic product.

If the content of the amino acid oil gelling agent is low, storage stability is poor, and if the content is high, there is a tendency that usability is inferior, while if the content of the amino acid oil gelling agent is within the above-described range, sufficient storage stability and excellent usability are obtained, so that it is preferable.

The polyamide resin used in the present invention is not limited specifically, but an amide-terminated polyamide resin or an ester-terminated polyamide resin represented by the following general formula (2)

[Chem. 4]

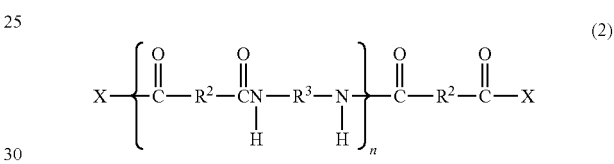

(2)

(wherein, X represents $-N(R^1)_2$ group or $-OR^1$ group, wherein $R^1$ represents $C_8$ to $C_{22}$ linear chain or branched chain alkyl group which may be the same or different from each other, $R^2$ represents a dimer acid residue, $R^3$ represents an ethylenediamine residue, n represents an integer from 2 to 4.) is preferable. Two or more of the above-described amide-terminated polyamide resins and ester-terminated polyamide resins may be used in combination.

In the above general formula (2), $R^1$ may be a straight-chain or a branched-chain alkyl group; as the straight-chain alkyl group, $C_8$: octyl group, $C_{10}$: decyl group, $C_{12}$: lauryl group, $C_{14}$: myristyl group, $C_{16}$: palmityl group, $C_{18}$: stearyl group, $C_{20}$: arachidyl group, and $C_{22}$: behenyl group, etc. are exemplified. Also, among these, as a branched-chain alkyl group, $C_8$: 2-ethylhexyl group, $C_9$: isononyl group, $C_{10}$: isodecyl group, $C_{13}$: isotridecyl group, and $C_{18}$: isostearyl group, etc. are exemplified. Of these, $C_8$ to $C_{20}$ alkyl group is preferable, $C_{14}$ to $C_{20}$ alkyl group is more preferable, and $C_{14}$ to $C_{18}$ alkyl group is the most preferable.

In the above general formula (2), as $R^2$, dimer dilinoleic acid residue that is a dimeric acid residue, and the residues of adipic acid, pimelic acid, suberic acid, azelaic acid, sebacic acid, undecane dioic acid, dodecane dioic acid, tridecane dioic acid, tetradecane dioic acid, pentadecane dioic acid, octadecane dioic acid, nonadecane dioic acid and eicosane dioic acid that are dibasic acids, etc. are included. Among these examples, dimer dilinoleic acid residue is the most preferable.

As the specific examples of the above preferable polyamide resin, HAIMALATE PAM, RISOCAST PAM66, SYLVACLEAR A200V and A2614V as examples of the amide-terminated polyamide resin, and UNICLEAR 100VG and C75V as the example of the ester-terminated polyamide resin are included, but the specific polyamide resin used in the present invention is not limited thereto.

The content of the polyamide resin is not limited specifically; from the viewpoint of solidification property, it is preferably 0.5 to 70 mass %, more preferably 1 to 65 mass %, even more preferably 1.5 to 63 mass % of the entire cosmetic.

If the content of the polyamide resin is low, the storage stability is poor, and if its content is high, there is a tendency that usability is inferior, whereas if the content of the polyamide resin is within the above-described range, sufficient storage stability and excellent usability can be obtained, therefore it is preferable.

The monoester used in the present invention is the monoester having a $C_9$ to $C_{24}$ linear chain or branched chain fatty acid residue, the monoester having a $C_9$ to $C_{24}$ linear chain or branched chain alcohol residue, or the monoester having a $C_9$ to $C_{24}$ linear chain or branched chain fatty acid residue and a $C_9$ to $C_{24}$ linear chain or branched chain alcohol residue.

If the carbon numbers of the linear chain or branched chain fatty acid residue and the alcohol residue that is possessed by these monoesters become $C_8$ or less at the same time, that is, if the carbon number of the monoester molecule becomes 16 or less, there is a tendency that irritating nature against skin becomes strong. Further, if the carbon number of the linear chain or branched chain fatty acid residue or the alcohol residue that is possessed by these monoesters becomes $C_{25}$ or more, there is a tendency that the compatibility with a polyamide resin etc. is decreased.

Therefore, as to the monoester used, high safety and good storage stability etc. can be obtained as far as it is in the range of a monoester having a $C_9$ to $C_{24}$ linear chain or branched chain fatty acid residue and/or a $C_9$ to $C_{24}$ linear chain or branched chain alcohol residue, so that it is preferable. Two or more of these monoesters may be used in combination.

Specifically, isononyl isononanoate, isodecyl isononanoate, isotridecyl isononanoate, 2-ethylhexyl isononanoate, etc., that are isononanoate esters, cetyl ethylhexanoate, hexyldecyl ethylhexanoate, isononyl ethylhexanoate, etc., that are 2-ethylhexanoate esters, isopropyl myristate, isocetyl myristate, octyldodecyl myristate, etc., that are myristate esters, ethyl isostearate, isopropyl isostearate, hexyldecyl isostearate, isostearyl isostearate, cholesteryl isostearate, phytosteryl isostearate etc., that are isostearate esters, isostearyl lactate, ocryldodecyl lactate, etc., that are lactate esters, ethylhexyl hydroxystearate, octyl hydroxystearate, phytosteryl hydroxystearate, cholesteryl hydroxystearate, etc., that are hydroxystearate esters, oleyl oleate, phytosteryl oleate, octyldodecyl oleate, etc., that are oleate esters, isodecyl neopentanoate, isostearyl neopentanoate, octyldodecyl neopentanoate, etc., that are neopentanoate esters, isopropyl palmitate, ethylhexyl palmitate, etc., that are palmitate esters, hexyl laurate, etc. that are laurate esters, isocetyl stearate etc. that are stearate esters, hexyldecyl neodecanoate, octyldodecyl neodecanoate, etc. that are neodecanoate esters, ethyl nonanoate, cholesteryl nonanoate, octyl nonanoate, etc. that are nonanoate (pelargonate) esters, can be mentioned, in addition to these, octyldodecyl ricinoleate, oleyl erucate, octyldodecyl erucate, lauroyl sarcosine isopropyl, etc. can be mentioned.

Among the above-described monoesters, from the viewpoint of safety, storage stability, etc., more preferably, isononyl isononanoate, isodecyl isononanoate, isotridecyl isononanoate, 2-ethylhexyl isononanoate, etc., that are isononanoate esters, cetyl ethylhexanoate, hexyldecyl ethylhexanoate, isononyl ethylhexanoate, etc. that are 2-ethylhexanoate esters can be mentioned, more preferably, isononyl isononanoate, isodecyl isononanoate, isotridecyl isononanoate, etc. that are isononanoate esters can be mentioned.

Though the content of the above-described monoester is not limited specifically, from the viewpoint of moderate hardness, etc., 10 to 90 mass % of the whole cosmetic is preferable, 15 to 85 mass % is more preferable, 20 to 80 mass % is further preferable.

If the content of the monoester is low, there is a tendency that usability is inferior, and if the content thereof is high, there is a tendency that shape retention property is inferior, whereas if the content of the monoester is within the above-described range, sufficient usability and excellent shape retention property can be obtained, so that it is preferable.

In the cosmetic of the present invention, another oil agent may be further contained as other ingredients. Another oil agent preferably used in the present invention is not limited specifically, and the following are exemplified. One or more of these oil agents may be used in combination.

As animal and vegetable fats, hydrogenated animal and vegetable fats, for example, avocado oil, nettle tree oil, olive oil, cacao fat, Japanese nutmeg oil, apricot kernel oil, hardened oil, wheat germ oil, sesame oil, rice germ oil, rice bran oil, sugarcane wax, sasanqua oil, safflower oil, shea butter, Paulownia fagesii oil, cinnamon oil, soybean oil, tea berry oil, camellia oil, evening primrose oil, cone oil, rapeseed oil, germ oil, palm oil, palm core oil, castor oil, hardened castor oil, sunflower oil, grapefruit oil, simmondsia chenensis (jojoba) seed oil, macadamia nut oil, beeswax, cottonseed oil, cotton wax, Japan wax, montan wax, palm tree oil, hardened palm tree oil, earthnut oil, lanolin, liquid lanolin, reduced lanolin, lanolin alcohol, hard lanolin, lanolin acetate, lanolin fatty acid isopropyl, etc. are exemplified.

As hydrocarbon oils, ozokerite, squalane, squalene, ceresin, paraffin, paraffin wax, liquid paraffin, pristane, polyisobutylene, microcrystalline wax, Vaseline, etc. are exemplified, as higher fatty acids, lauric acid, myristic acid, palmitic acid, stearic acid, behenic acid, undecylenoic acid, oleic acid, linoleic acid, linolenic acid, arachidonic acid, eicosapentaenoic acid (EPA), docosahexaenoic acid (DHA), isostearic acid, 12-hydroxystearic acid, etc. are exemplified.

As diester oils, diisobutyl adipate, diisopropyl adipate, diethylhexyl succinate, neopentyl glycol diisononanoate, neopentyl glycol diethylhexanoate, neopentyl glycol dicaprate, diisostearyl malate, diisopropyl dilinoleate, ethyleneglycol dioctanoate, octyldodecyl stearoyloxystearate, diisopropyl sebacate, di(cholesteryl/octyldodecyl) lauroyl glutamate, di(phytosteryl/octyldodecyl) lauroyl glutamate, etc. are exemplified.

As triester oils, triethylhexanoin, trimethylolpropane triethylhexanoate, glyceryl tri(caprylate/caprate), triisostearin, trimethylolpropane triisostearate, erythrityl triethylhexanoate, etc. are exemplified, as tetraesters, pentaerythrityl tetraethylhexanoate, pentaerythrityl tetraisostearate, etc. are exemplified.

As polyester oils, polyglyceryl-2 isostearate, polyglyceryl-2 diisostearate, polyglyceryl-2 triisostearate, polyglyceryl-2 tetraisostearate, etc. that are polyglycerin fatty acid esters are exemplified.

As high viscosity ester oil agents, (hydroxystearic acid/stearic acid/resin acid) dipentaerythrityl, isostearic acid hydrogenated castor oil, dimer dilinoleic acid hydrogenated castor oil, (polyglyceryl-2 isostearate/dimer dilinoleic acid) copolymer, dimer dilinoleic acid (phytosteryl/isostearyl/cetyl/stearyl/behenyl), dimer dilinoleic acid dimer dilinoleyl bis(phytosteryl/behenyl/isostearyl), dimer dilinoleic acid di(isostearyl/phytosteryl), dimer dilinoleyl hydrogenated rosin condensate, dimer dilinoleyl diisostearate, dimer dilinoleyl dimer dilinoleate, di(cholesteryl/behenyl/octyldodecyl) lauroyl glutamate, di(octyldodecyl/phytosteryl/behenyl) lauroyl glutamate, myristoyl methylalanine (phytosteryl/decyl tetradecyl), (diglycerin/dilinoleic acid/hydroxystearic acid) copolymer etc. are exemplified.

Alcohols preferably used in the present invention are not limited specifically, and the followings are exemplified. One or more of these alcohols may be used in combination.

As branched alcohols, the one with 10 to 40 carbon atoms, hexyl decanol, isostearyl alcohol, octyl dodecanol, decyl tetradecanol, dodecyl hexadecanol, tetradecyl octadecanol, hexadecyl eicosanol are exemplified, octyl dodecanol being the most preferable.

As divalent alcohols, butylene glycol, pentylene glycol, propylene glycol, dipropylene glycol, hexylene glycol, octylene glycol, and polypropylene glycol having the average molecular weight of 200 to 2000, etc. are exemplified.

As higher alcohols, the ones with 7 or more carbon atoms are preferable, the ones with 10 or more carbon atoms are more preferable, and the ones with 15 or more carbon atoms are even more preferable. As to the higher alcohols used in the present invention, lauryl alcohol, myristyl alcohol, stearyl alcohol, eicosanol, behenyl alcohol, oleyl alcohol, cetostearyl alcohol, cholesterol, phytosterol, POE cholesterol ether, monostearyl glycerin ether (batyl alcohol), monooleyl glyceryl ether (selachyl alcohol), cetanol, etc. are exemplified.

The cosmetic of the present invention further comprising a silicone oil or a thickening agent as other ingredients is preferable from the viewpoint of solidification property and skin moisturizing property.

The silicone oil used in the present invention is not specifically limited; silicone compounds, such as dimethyl polysiloxane, methylphenyl polysiloxane, alkyl denatured organopolysiloxane, terminal denatured organopolysiloxane, fluorine denatured organopolysiloxane, amodimethicone, amino denatured organopolysiloxane, volatile silicone, alkyldimethicone, etc. are exemplified but methylphenyl polysiloxane and dimethyl polysiloxane with excellent general versatility are preferable.

The amount of the silicone oil used in the present invention is not specifically limited as well; from the viewpoint of solidification property and skin moisturizing property the amount is preferably 0.1 to 20 mass % of the entire cosmetic, more preferably 1 to 15 mass %, and most preferably 2 to 10 mass %.

The thickening agent used in the present invention are not specifically limited as well; natural and artificial thickening agents, etc., such as alginic acid, polyaspartic acid, deoxyribo nucleic acid and salts thereof, guar gum, agar-agar, gelatin, sodium polyacrylate, cellulose ester, calcium alginate, carboxyvinyl polymer, ethylene/acrylic acid copolymer, vinylpyrrolidone polymer, vinyl alcohol/vinylpyrrolidone copolymer, nitrogen substituted acrylamide polymer, polyacrylamide, cationized guar gum, dimethylacrylammonium polymer, acrylic acid-acryl metacrylate copolymer, POE/POP copolymer, polyvinyl alcohol, pullulan, tamarind seed polysaccharides, xanthan gum, carrageenan, high methoxyl pectin, low methoxyl pectin, gum arabic, crystalline cellulol, arabinogalactan, karaya gum, tragacanth gum, albumin, casein, curdlan, gellan gum, dextrin fatty acid ester, cellulose, polyethyleneimine, highly polymerized polyethylene glycol, cationized silicone polymer, synthetic latex, alkyl dimethicone or silicone polyamide copolymer with 18 or more carbon atoms that is a silicon gelling agent, (behenic acid eicosandioic acid)glyceryl, (behenic acid eicosandioic acid) polyglyceryl-10, (vinyl caprolactam/VP/dimethylaminoethyl methacrylate)copolymer, etc. are exemplified.

Furthermore, in the cosmetic of the present invention, various ingredients can be used such as ultraviolet absorbing agents, ultraviolet scattering agents, oil agents, thickening gelling agents, surfactants, antiseptic agents, antimicrobials, fragrances, humectants, salts, solvents, antioxidants, chelating agents, neutralizing agents, pH regulators, insect rejectants, bioactive ingredients, etc. that are usually used in the oily cosmetic.

As the bioactive ingredients used in the present invention, materials giving certain bioactivities to skin when applied to skin are exemplified. For example, anti-inflammatory agents, antiaging agents, tightening agents, antioxidative agents, humectants, blood circulation accelerators, antimicrobials, microbicides, desiccants, cool sense agents, warm sense agents, vitamins, amino acids, wound healing accelerators, torpents, analgesics, cell activator agents, enzyme ingredients, etc. are exemplified. According to the present invention, one or more of these bioactive ingredients are preferably blended.

The present invention relates also to a method for making the above-described cosmetic; the method is not limited specifically, and known method can be employed properly, and the method comprises the step of mixing one or more amino acid oil gelling agents, one or more polyamide resins, and one or more monoesters selected from the monoesters having a $C_9$ to $C_{24}$ linear chain or branched chain fatty acid residue and/or a $C_9$ to $C_{24}$ linear chain or branched chain alcohol residue.

A cosmetic product having improved sense of use and storage stability can be obtained by blending the cosmetic of the present invention to a cosmetic product.

The form of the cosmetic product according to the present invention is not limited, and for example, selected from an antiperspirant, a cream, a lip gloss, an eye shadow, a mascara, a lip stick, a hair gel, a hair wax, a hair stick, a hair cream, a sun protection product, a foundation, an eye color, etc., and can be made suitable in each application.

The present invention relates also to a method for increasing usability and storage stability of a cosmetic; the method comprises the step of mixing one or more amino acid oil gelling agents, one or more polyamide resins, and one or more monoesters selected from the monoesters having a $C_9$ to $C_{24}$ linear chain or branched chain fatty acid residue and/or a $C_9$ to $C_{24}$ linear chain or branched chain alcohol residue.

As one or more amino acid oil gelling agents, amino acid oil gelling agents represented by the above general formula (1) are preferable, one or more amino acid oil gelling agents comprising at least dibutyl lauroyl glutamide are more preferable. Also, as one or more polyamide resins, the amide-terminated polyamide resin and ester-terminated polyamide resin represented by the above general formula (2) are preferable. Further, as the above-described specific monoester, one or more monoesters selected from the group consisting of isononanoate ester, 2-ethylhexanoate ester, myristate ester, isostearate ester, lactate ester, hydroxystearate ester, oleate ester, neopentanoate ester, palmitate ester, laurate ester, stearate ester, neodecanoate ester, and nonanoate ester are preferable.

According to the method of the present invention, a cosmetic having superior usability and storage stability to the prior products can be obtained.

EXAMPLES

Hereinafter, the present invention is further specifically explained by means of Examples and Comparative examples relating to the cosmetic of the present invention, but the present invention should not be limited by any way thereby, and various change is possible within the range without departure from the technical idea of the present invention. Furthermore, unless specified otherwise, "%" described below means "mass %".

Examples 1 to 7

(Making of Lip Glosses)

Making of various lip glosses consisting of each composition shown in Tables 1 to 7 below was carried out by a routine method. As an example, each ingredient shown in Table 1 below was mixed in predetermined amounts, which was then dissolved at about 110° C. with stirring to make a uniform mixture. This mixture was cooled to about 30° C. to obtain a lip gloss composition of Example 1.

[Table 1]

TABLE 1

Palette type lip gloss (Example 1)

| | Name of Ingredient | Compounding Amount (%) |
|---|---|---|
| 1 | Dibutyl lauroyl glutamide | 1.50 |
| 2 | Polyamide resin | 4.00 |
| 3 | Isononyl isononanoate | 1.50 |
| 4 | Polyglyceryl-2 diisostearate | 28.00 |
| 5 | Diisostearyl malate | 15.00 |
| 6 | Pentaerythrytyl tetraisostearate | 10.00 |
| 7 | Octyl dodecanol | 3.00 |
| 8 | (Polyglyceryl-2 isostearate/dimer dilinoleic acid) copolymer | 36.69 |
| 9 | Red No. 226 (C.I. 73360) | 0.01 |
| 10 | Synthetic bronze mica, titanium oxide, iron oxide [lame material] | 0.30 |
| | Total | 100.00 |

[Table 2]

TABLE 2

Palette type lip gloss (Example 2)

| | Name of Ingredient | Compounding Amount (%) |
|---|---|---|
| 1 | Dibutyl lauroyl glutamide | 0.40 |
| 2 | Polyamide resin | 6.00 |
| 3 | Ethylhexyl hydroxystearate | 20.50 |
| 4 | Hexyldecyl ethylhexanoate | 3.05 |
| 5 | Polyglyceryl-2 diisostearate | 15.00 |
| 6 | Polyglyceryl-2 triisostearate | 5.00 |
| 7 | Diisostearyl malate | 8.00 |
| 8 | (Polyglyceryl-2 isostearate/dimer dilinoleic acid) copolymer | 30.00 |
| 9 | Hydrogenated polyisobutene | 10.00 |
| 10 | Synthetic wax | 0.30 |
| 11 | Titanium oxide | 0.10 |
| 12 | Red No. 202 (C.I. 15850:1) | 1.20 |
| 13 | Blue No. 1 aluminum lake (C.I. 42090) | 0.05 |
| 14 | (PET/Methyl polymethacrylate) laminate [lame material] | 0.40 |
| | Total | 100.00 |

[Table 3]

TABLE 3

Lip gloss (Example 3)

| | Name of Ingredient | Compounding Amount (%) |
|---|---|---|
| 1 | Dibutyl lauroyl glutamide | 0.30 |
| 2 | Polyamide resin | 1.50 |
| 3 | Isotridecyl isononanoate | 3.30 |
| 4 | Polyglyceryl-2 diisostearate | 22.55 |
| 5 | Diisostearyl malate | 12.90 |
| 6 | Pentaerythrytyl tetraisostearate | 8.00 |
| 7 | Neopentyl glycol diisononanoate | 5.00 |
| 8 | (Polyglyceryl-2 isostearate/dimer dilinoleic acid) copolymer | 30.00 |
| 9 | Dimer dilinoleic acid hydrogenated castor oil | 10.00 |
| 10 | Phenyl trimethicone | 3.00 |

TABLE 3-continued

Lip gloss (Example 3)

| | Name of Ingredient | Compounding Amount (%) |
|---|---|---|
| 11 | Titanium oxide | 1.50 |
| 12 | Iron oxide [colcothar] | 1.50 |
| 13 | Red No. 201 (C.I. 15850) | 0.10 |
| 14 | Blue No. 1 aluminum lake (C.I. 42090) | 0.05 |
| 15 | Synthetic bronze mica, titanium oxide, iron oxide [lame material] | 0.30 |
| | Total | 100.00 |

[Table 4]

TABLE 4

Lip gloss (Example 4)

| | Name of Ingredient | Compounding Amount (%) |
|---|---|---|
| 1 | Dibutyl lauroyl glutamide | 0.50 |
| 2 | Polyamide resin | 1.70 |
| 3 | Ethylhexyl isononanoate | 11.15 |
| 4 | Polyglyceryl-2 diisostearate | 21.00 |
| 5 | Diisostearyl malate | 14.63 |
| 6 | Diisopropyl dilinoleate | 10.00 |
| 7 | (Polyglyceryl-2 isostearate/dimer dilinoleic acid) copolymer | 30.00 |
| 8 | Isostearic acid hydrogenated castor oil | 5.00 |
| 9 | *Simmondsia chenensis* (Jojoba) seed oil | 1.00 |
| 10 | Squalane | 3.00 |
| 11 | (Palmitic acid/ethylhexanoic acid) dextrin | 1.00 |
| 12 | Carmine | 0.02 |
| 13 | Titanium oxide, mica [pearl agent] | 1.00 |
| | Total | 100.00 |

[Table 5]

TABLE 5

Lip gloss (Example 5)

| | Name of Ingredient | Compounding Amount (%) |
|---|---|---|
| 1 | Dibutyl lauroyl glutamide | 0.35 |
| 2 | Polyamide resin | 1.80 |
| 3 | Ethylhexyl hydroxystearate | 22.24 |
| 4 | Isostearyl neopentanoate | 5.40 |
| 5 | Polyglyceryl-2 diisostearate | 15.00 |
| 6 | Polyglyceryl-2 triisostearate | 6.00 |
| 7 | Diisostearyl malate | 8.00 |
| 8 | Dimer dilinoleic acid hydrogenated castor oil | 10.00 |
| 9 | Hexa(hydroxystearic acid/stearic acid/rosin acid) dipentaerythrityl | 10.00 |
| 10 | Hydrogenated polyisobutene | 20.00 |
| 11 | Titanium oxide | 0.20 |
| 12 | Red No. 201 (C.I. 15850) | 0.60 |

TABLE 5-continued

Lip gloss (Example 5)

| | Name of Ingredient | Compounding Amount (%) |
|---|---|---|
| 13 | Red No. 202 (C.I. 15850:1) | 0.01 |
| 14 | (PET/Methyl polymethacrylate) laminate [lame material] | 0.40 |
| | Total | 100.00 |

[Table 6]

TABLE 6

Transparent lip gloss (Example 6)

| | Name of Ingredient | Compounding Amount (%) |
|---|---|---|
| 1 | Dibutyl lauroyl glutamide | 0.50 |
| 2 | Polyamide resin | 2.80 |
| 3 | Hexyldecyl ethylhexanoate | 5.00 |
| 4 | Polyglyceryl-2 diisostearate | 20.00 |
| 5 | Diisostearyl malate | 20.00 |
| 6 | Trimethylolpropane triethylhexanoate | 11.60 |
| 7 | (Polyglyceryl-2 isostearate/dimer dilinoleic acid) copolymer | 40.00 |
| 8 | d-δ-tocopherol | 0.10 |
| | Total | 100.00 |

[Table 7]

TABLE 7

Transparent lip gloss (Colored) (Example 7)

| | Name of Ingredient | Compounding Amount (%) |
|---|---|---|
| 1 | Dibutyl lauroyl glutamide | 0.35 |
| 2 | Polyamide resin | 1.50 |
| 3 | Isopropyl myristate | 15.00 |
| 4 | Polyglyceryl-2 diisostearate | 10.00 |
| 5 | Polyglyceryl-2 triisostearate | 15.00 |
| 6 | Diisostearyl malate | 5.00 |
| 7 | Pentaerythrytyl tetraisostearate | 12.00 |
| 8 | (Polyglyceryl-2 isostearate/dimer dilinoleic acid) copolymer | 20.00 |
| 9 | Hydrogenated polyisobutene | 20.00 |
| 10 | Ethylhexyl methoxycinnamate | 0.50 |
| 11 | Red No. 218 (C.I. 45410:1) | 0.05 |
| 12 | Synthetic bronze mica, titanium oxide, iron oxide [lame material] | 0.60 |
| | Total | 100.00 |

Examples 8 to 11

(Making of Lipsticks)

Making of various lipsticks consisting of each composition shown in Tables 8 to 11 below was carried out by a routine method. As an example, each ingredient shown in Table 8 below was mixed in predetermined amounts, which was dissolved uniformly at 95 to 100° C. and defoamed. Then, this mixture was cast into an appropriate metallic mold, which was thereafter cooled to make a lipstick of Example 8.

[Table 8]

TABLE 8

Lipstick (Example 8)

| | Name of Ingredient | Compounding Amount (%) |
|---|---|---|
| 1 | Dibutyl lauroyl glutamide | 1.00 |
| 2 | Polyamide resin | 15.00 |
| 3 | Isotridecyl isononanoate | 23.50 |
| 4 | Ceresin | 1.50 |
| 5 | Microcrystalline wax | 1.50 |
| 6 | Diisostearyl malate | 15.00 |
| 7 | Octyl dodecanol | 8.00 |
| 8 | Polyglyceryl-2 diisostearate | 22.50 |
| 9 | (Polyglyceryl-2 isostearate/dimer dilinoleic acid) copolymer | 3.00 |
| 10 | Dimer dilinoleic acid hydrogenated castor oil | 3.00 |
| 11 | Pentaerythrytyl tetraisostearate | 6.00 |
| | Total | 100.00 |

[Table 9]

TABLE 9

Lipstick (Example 9)

| | Name of Ingredient | Compounding Amount (%) |
|---|---|---|
| 1 | Dibutyl lauroyl glutamide | 3.00 |
| 2 | Polyamide resin | 12.00 |
| 3 | Ethylhexyl hydroxystearate | 10.00 |
| 4 | Ocryldodecyl neopentanoate | 5.50 |
| 5 | Polyethylene | 4.50 |
| 6 | Decyl tetradecanol | 8.00 |
| 7 | Polyglyceryl-2 triisostearate | 20.00 |
| 8 | Neopentyl glycol diethylhexanoate | 19.00 |
| 9 | Hydrogenated polyisobutene | 10.90 |
| 10 | Triethyl hexanoin | 4.80 |
| 11 | Red No. 202 (C.I. 15850:2) | 0.10 |
| 12 | Titanium oxide-coated synthetic bronze mica | 1.00 |
| 13 | Mica titanium | 1.00 |
| 14 | Ethylhexyl methoxycinnamate | 0.10 |
| 15 | d-δ-tocopherol | 0.10 |
| | Total | 100.00 |

[Table 10]

TABLE 10

Transparent lipstick (Example 10)

| | Name of Ingredient | Compounding Amount (%) |
|---|---|---|
| 1 | Dibutyl lauroyl glutamide | 0.60 |
| 2 | Polyamide resin | 20.90 |
| 3 | Isotridecyl isononanoate | 22.50 |
| 4 | Polyglyceryl-2 diisostearate | 22.50 |
| 5 | Diisostearyl malate | 20.00 |
| 6 | Pentaerythrytyl tetraisostearate | 4.70 |
| 7 | (Diglycerin/dilinoleic acid/hydroxystearic acid) copolymer | 4.70 |

TABLE 10-continued

Transparent lipstick (Example 10)

| | Name of Ingredient | Compounding Amount (%) |
|---|---|---|
| 8 | Octyl dodecanol | 4.00 |
| 9 | d-δ-Tocopherol | 0.10 |
| | Total | 100.00 |

[Table 11]

TABLE 11

Transparent lipstick (Example 11)

| | Name of Ingredient | Compounding Amount (%) |
|---|---|---|
| 1 | Dibutyl lauroyl glutamide | 1.00 |
| 2 | Polyamide resin | 24.00 |
| 3 | Ethylhexyl hydroxystearate | 16.00 |
| 4 | Polyglyceryl-2 triisostearate | 23.00 |
| 5 | Neopentyl glycol diisononanoate | 23.00 |
| 6 | Isostearyl alcohol | 4.00 |
| 7 | (Polyglyceryl-2 isostearate/dimer dilinoleic acid) copolymer | 4.00 |
| 8 | Mineral oil | 4.00 |
| 9 | Synthetic bronze mica, titanium oxide, iron oxide [lame material] | 0.40 |
| 10 | Red No. 102 (C.I. 16255) | 0.20 |
| 11 | Water | 0.20 |
| 12 | Shikonin | 0.20 |
| | Total | 100.00 |

Example 12

(Making of Hair Stick)

Making of various hair sticks consisting of each composition shown in Table 12 below was carried out by a routine method. As an example, each ingredient shown in Table 12 below was mixed in predetermined amounts, which was dissolved uniformly at 95 to 100° C. and defoamed. Then, this mixture was cast into an appropriate case, which was thereafter cooled to make a hair stick of Example 12.

[Table 12]

TABLE 12

Transparent hair stick (Example 12)

| | Name of Ingredient | Compounding Amount (%) |
|---|---|---|
| 1 | Dibutyl lauroyl glutamide | 3.00 |
| 2 | Polyamide resin | 15.00 |
| 3 | Isotridecyl isononanoate | 45.00 |
| 4 | Ethylhexyl hydroxystearate | 12.00 |
| 5 | Diisostearyl malate | 15.00 |
| 6 | *Camellia* oil | 5.00 |
| 7 | *Simmondsia chenensis* (Jojoba) seed oil | 5.00 |
| | Total | 100.00 |

Examples 13 to 16

(Making of Various Cosmetic Products)

Making of various cosmetic products consisting of each composition shown in Tables 13 to 16 below was carried out by a routine method.

[Table 13]

TABLE 13

Foundation (Example 13)

| | Name of Ingredient | Compounding Amount (%) |
|---|---|---|
| 1 | Dibutyl lauroyl glutamide | 3.20 |
| 2 | Polyamide resin | 18.00 |
| 3 | Isononyl isononanoate | 17.00 |
| 4 | Ethylhexyl hydroxystearate | 1.50 |
| 5 | Polyglyceryl-2 triisostearate | 16.00 |
| 6 | Methyl polysiloxane | 15.00 |
| 7 | Diisostearyl malate | 10.00 |
| 8 | Mica titanium | 10.00 |
| 9 | Octyl dodecanol | 8.00 |
| 10 | Yellow iron oxide | 0.80 |
| 11 | Red iron oxide | 0.40 |
| 12 | Ultramarine blue | 0.10 |
| | Total | 100.00 |

[Table 14]

TABLE 14

Eye color (Example 14)

| | Name of Ingredient | Compounding Amount (%) |
|---|---|---|
| 1 | Dibutyl lauroyl glutamide | 2.40 |
| 2 | Polyamide resin | 15.00 |
| 3 | Cetyl ethylhexanoate | 6.00 |
| 4 | Glyceryl tri(caprylate/caprate) | 20.00 |
| 5 | Polyglyceryl-2 diisostearate | 15.00 |
| 6 | Diisostearyl malate | 13.00 |
| 7 | Octyl dodecanol | 10.00 |
| 8 | Mica titanium | 10.00 |
| 9 | (Polyglyceryl-2 isostearate/dimer dilinoleic acid) copolymer | 5.00 |
| 10 | Methylphenyl polysiloxane | 3.00 |
| 11 | Yellow iron oxide | 0.30 |
| 12 | Ultramarine blue | 0.10 |
| 13 | Red No. 226 (C.I. 73360) | 0.10 |
| 14 | Red iron oxide | 0.10 |
| | Total | 100.00 |

[Table 15]

TABLE 15

Antiperspirant (Example 15)

| | Name of Ingredient | Compounding Amount (%) |
|---|---|---|
| 1 | Dibutyl lauroyl glutamide | 1.80 |
| 2 | Polyamide resin | 16.20 |
| 3 | Isononyl isononanoate | 20.00 |
| 4 | Polyglyceryl-2 diisostearate | 30.00 |
| 5 | Methylphenyl polysiloxane | 15.00 |
| 6 | Octyl dodecanol | 10.00 |
| 7 | Methyl polysiloxane | 3.00 |
| 8 | Ceresin | 1.50 |

TABLE 15-continued

Antiperspirant (Example 15)

| | Name of Ingredient | Compounding Amount (%) |
|---|---|---|
| 9 | Polyethylene | 1.50 |
| 10 | Fragrance | 1.00 |
| | Total | 100.00 |

[Table 16]

TABLE 16

Hair gel (Example 16)

| | Name of Ingredient | Compounding Amount (%) |
|---|---|---|
| 1 | Dibutyl lauroyl glutamide | 1.50 |
| 2 | Polyamide resin | 11.50 |
| 3 | Cetyl ethylhexanoate | 5.00 |
| 4 | Diisostearyl malate | 36.36 |
| 5 | Polyglyceryl-2 isostearate | 15.64 |
| 6 | Pentaerythrytyl tetraisostearate | 16.00 |
| 7 | Dimethicone | 5.00 |
| 8 | Octyl dodecanol | 5.00 |
| 9 | Cyclomethicone | 4.00 |
| | Total | 100.00 |

(Property Evaluation Method)

The cosmetic products consisting of each composition of Tables 17 to 20 below (Examples and Comparative examples) were made, and evaluations of various properties thereof were carried out. The items of property evaluations and test methods are shown below.

(1) Spreadability

Measurement was carried out using a friction sense tester, a sample fixture and artificial leather. The sample was fixed perpendicularly downwards by the fixture, the sample side was applied to and from three times on the same part of the surface of the artificial leather at a constant speed, and the average friction coefficient was measured. Herein, sample table and artificial leather were kept at the temperature of 35° C.

(2) Adhesive property

Measurement was carried out using a friction sense tester, a sample fixture, artificial leather and a scale for analysis. The sample was fixed perpendicularly downwards by the fixture, the sample side was applied to and from three times on the same part of the surface of the artificial leather at a constant speed, and the average value of each adhesion amount was measured. Herein, sample table and artificial leather were kept at the temperature of 35° C.

(3) Storage stability

As to a sample after having stored in temperature-controlled room of 45° C. for three months and a sample after having stored in temperature-controlled room shuttling between −5° C. and 45° C. for a period to shuttle five times, the appearance such as separation and sweating state was observed visually.

(4) Shape retention property

Evaluation was carried out by measuring the hardness of the samples stored in a low temperature (5° C.), normal temperature (25° C.) and a high temperature (35° C.), respectively. Hardness was measured by using a hardness meter.

(5) Appearance

Using a visible-ultraviolet spectrophotometer, the transmissivity in the visible light range (wavelength 400 to 800 nm) of the sample was measured.

(6) Ease of preparation

Solubility and ease of using (handling property) etc. of each ingredient were confirmed at the time of preparation of a cosmetic product of each composition of Examples and Comparative examples.

As to evaluation of each of above-described property, evaluation was carried out relatively based on the below criteria from the measurement result of all samples of Examples and Comparative examples.

5 . . . Good (○)
4 . . . Basically good (Δ to ○)
3 . . . Average (Δ)
2 . . . slightly bad (X to Δ)
1 . . . bad (X)

Examples 1-1 to 4-1 and Comparative Examples 1-1 to 4-1

Transparent hair sticks of Examples and Comparative examples consisting of each composition of Tables 17 and 18 below was made by a similar method to the above-mentioned Example 12, and evaluations of various properties thereof were carried out by the above-described test method. The one prepared and shaped and thereafter allowed to stand at 25° C. for 25 hours was served as a sample for each test. The results are shown in Tables 17 and 18.

[Table 17]

TABLE 17

Transparent hair stick (Examples)

| | | Examples | | | |
|---|---|---|---|---|---|
| | Name of Ingredient | 1-1 | 2-1 | 3-1 | 4-1 |
| 1 | Dibutyl lauroyl glutamide | 1.00 | 1.00 | 2.00 | 4.00 |
| 2 | Polyamide resin | 20.00 | 19.80 | 17.50 | 22.60 |
| 3 | Dextrin palmitate | | | | 0.5 |
| 4 | Ethylhexyl hydroxystearate | 4.00 | 14.20 | 8.00 | 11.90 |
| 5 | Isotridecyl isononanoate | 45.0 | 47.50 | 40.00 | 38.00 |
| 6 | Isopropyl myristate | | 10.00 | | 16.00 |
| 7 | Octyl dodecyl neopentanoate | | 5.00 | | |
| 8 | Polyglyceryl-2 diisostearate | | | | |
| 9 | Diisostearyl malate | 20.00 | | 17.50 | |
| 10 | Neopentyl glycol diisononanoate | | | | 7.00 |
| 11 | Cyclopentasiloxane | 5.00 | | | |
| 12 | Dimethicone | 5.00 | | | |
| 13 | *Camellia* oil | | | 5.00 | |

TABLE 17-continued

Transparent hair stick (Examples)

| | Name of Ingredient | | | Examples 1-1 | 2-1 | 3-1 | 4-1 |
|---|---|---|---|---|---|---|---|
| 14 | *Simmondsia chenensis* (Jojoba) seed oil | | | | | 5.00 | |
| 15 | (Polyglyceryl-2 isostearate/dimer dilinoleic acid) copolymer | | | | 2.50 | 5.00 | |
| | Total | | | 100.00 | 100.00 | 100.00 | 100.00 |
| Evaluation items | Usability | Spreadability | Ease of coating | 5 | 5 | 5 | 4 |
| | | Adhesive property | Sense of non-tackiness, adhesive feeling | 5 | 5 | 5 | 3 |
| | | Storage stability | Presence or absence of separating and sweating | 5 | 5 | 5 | 4 |
| | | Shape retention property | Moderate hardness | 5 | 5 | 5 | 5 |
| | | Appearance | Transparency | 5 | 5 | 5 | 4 |
| | | Ease of preparation | Ease of dissolution, ease of use | 5 | 5 | 5 | 3 |

[Table 18]

TABLE 18

Transparent hair stick (Comparative examples)

| | Name of Ingredient | | | Comparative examples 1-1 | 2-1 | 3-1 | 4-1 |
|---|---|---|---|---|---|---|---|
| 1 | Dibutyl lauroyl glutamide | | | | 1.00 | 2.00 | 4.00 |
| 2 | Polyamide resin | | | 15.00 | 19.80 | 17.50 | |
| 3 | Dextrin palmitate | | | | | | |
| 4 | Ethylhexyl hydroxystearate | | | | | | 11.90 |
| 5 | Isotridecyl isononanoate | | | 65.0 | | | 38.00 |
| 6 | Isopropyl myristate | | | | | | |
| 7 | Octyl dodecyl neopentanoate | | | | | | |
| 8 | Polyglyceryl-2 diisostearate | | | | 47.50 | 17.50 | |
| 9 | Diisostearyl malate | | | 15.00 | | | 22.60 |
| 10 | Neopentyl glycol diisononanoate | | | | 14.20 | 40.00 | 7.00 |
| 11 | Cyclopentasiloxane | | | | | | |
| 12 | Dimethicone | | | 5.00 | | | |
| 13 | *Camellia* oil | | | | 10.00 | 5.00 | |
| 14 | *Simmondsia chenensis* (Jojoba) seed oil | | | | | 13.00 | |
| 15 | (Polyglyceryl-2 isostearate/dimer dilinoleic acid) copolymer | | | | 7.50 | 5.00 | 16.50 |
| | Total | | | 100.00 | 100.00 | 100.00 | 100.00 |
| Evaluation items | Usability | Spreadability | Ease of coating | 4 | 2 | 2 | 2 |
| | | Adhesive property | Sense of non-tackiness, adhesive feeling | 4 | 2 | 3 | 2 |
| | | Storage stability | Presence or absence of separating and sweating | 1 | 1 | 3 | 2 |
| | | Shape retention property | Moderate hardness | 4 | 4 | 4 | 2 |
| | | Appearance | Transparency | 1 | 3 | 1 | 2 |
| | | Ease of preparation | Ease of dissolution, ease of use | 5 | 4 | 3 | 1 |

As shown in Tables 17 and 18, it can be seen that the transparent hair stick containing the cosmetic according to Examples 1-1 to 4-1 blended with an amino acid oil gelling agent, a polyamide resin and a specific monoester have as well as excellent usability such as ease of coating, sense of non-tackiness, adhesive feeling, and sufficient storage stability, and also have high shape retention property and excellent appearance (high transparency).

To the contrary, it can be seen that Comparative example 1-1 that does not contain an amino acid oil gelling agent, Comparative example 4-1 that does not contain a polyamide resin, and Comparative examples 2-1 and 3-1 that do not contain a specific monoester were inferior in usability such as ease of coating, sense of non-tackiness, and adhesive feeling, storage stability, shape retention property and appearance (transparency) to Examples 1-1 to 4-1, and in particular storage stability is extremely low and transparency is largely inferior.

Examples 1-2 to 4-2 and Comparative Examples 1-2 to 4-2

Transparent lipsticks of Examples and Comparative examples having each composition of Tables 19 and 20 below were made according to a similar method to above-mentioned Example 8, and evaluations of each property thereof were carried out in accordance with the above-described test method. After making and shaping, the ones allowed to stand at 25° C. for 24 hours were served as samples for each test. The results are shown in Tables 19 and 20.

[Table 19]

TABLE 19

Transparent lipsticks (Examples)

| | | | | Examples | | | |
|---|---|---|---|---|---|---|---|
| | Name of Ingredient | | | 1-2 | 2-2 | 3-2 | 4-2 |
| 1 | Dibutyl lauroyl glutamide | | | 1.00 | 3.00 | 2.00 | 2.00 |
| 2 | Polyamide resin | | | 17.50 | 20.00 | 17.50 | 19.80 |
| 3 | Dextrin palmitate | | | | | | 0.10 |
| 4 | Ethylhexyl hydroxystearate | | | 4.00 | 7.00 | 8.00 | 10.20 |
| 5 | Isotridecyl isononanoate | | | 60.00 | 40.00 | 45.00 | 50.00 |
| 6 | Isopropyl myristate | | | | 12.00 | | 8.90 |
| 7 | Polyglyceryl-2 triisostearate | | | | 5.00 | | |
| 8 | Diisostearyl malate | | | 17.50 | 10.00 | 17.50 | |
| 9 | Pentaerythrytyl tetraisostearate | | | | | | 7.00 |
| 10 | Octyl dodecanol | | | | 1.50 | 5.00 | |
| 11 | Squalane | | | | | 5.00 | |
| 12 | (Polyglyceryl-2 isostearate/dimer dilinoleic acid) copolymer | | | | 1.50 | | |
| 13 | Hydrogenated polyisobutene | | | | | | 2.00 |
| | Total | | | 100.00 | 100.00 | 100.00 | 100.00 |
| Evaluation items | Usability | Spreadability | Ease of coating | 5 | 5 | 5 | 5 |
| | | Adhesive property | Sense of non-tackiness, adhesive feeling | 5 | 5 | 5 | 5 |
| | Storage stability | | Presence or absence of separating and sweating | 5 | 5 | 5 | 5 |
| | Shape retention property | | Moderate hardness | 5 | 5 | 5 | 5 |
| | Appearance | | Transparency | 5 | 5 | 4 | 3 |
| | Ease of preparation | | Ease of dissolution, ease of use | 5 | 3 | 4 | 4 |

[Table 20]

TABLE 20

Transparent lipsticks (Comparative examples)

| | | Comparative examples | | | |
|---|---|---|---|---|---|
| | Name of Ingredient | 1-2 | 2-2 | 3-2 | 4-2 |
| 1 | Dibutyl lauroyl glutamide | | 5.00 | 2.00 | |
| 2 | Polyamide resin | 25.50 | | 17.50 | 15.00 |
| 3 | Dextrin palmitate | | | | 2.10 |
| 4 | Ethylhexyl hydroxystearate | | 20.00 | | |
| 5 | Isotridecyl isononanoate | 44.50 | | | 50.00 |
| 6 | Isopropyl myristate | | | | |
| 7 | Polyglyceryl-2 triisostearate | | | 45.00 | |
| 8 | Diisostearyl malate | | | | 15.00 |
| 9 | Pentaerythrytyl tetraisostearate | | 35.00 | 17.50 | 7.00 |

TABLE 20-continued

Transparent lipsticks (Comparative examples)

| | | | | Comparative examples | | | |
|---|---|---|---|---|---|---|---|
| | Name of Ingredient | | | 1-2 | 2-2 | 3-2 | 4-2 |
| 10 | Octyl dodecanol | | | 30.00 | | 5.00 | |
| 11 | Squalane | | | | 34.00 | 5.00 | 8.00 |
| 12 | (Polyglyceryl-2 isostearate/dimer dilinoleic acid) copolymer | | | | | 8.00 | |
| 13 | Hydrogenated polyisobutene | | | | 6.00 | | 2.90 |
| | Total | | | 100.00 | 100.00 | 100.00 | 100.00 |
| Evaluation items | Usability | Spreadability | Ease of coating | 4 | 3 | 3 | 3 |
| | | Adhesive property | Sense of non-tackiness, adhesive feeling | 5 | 3 | 3 | 4 |
| | | Storage stability | Presence or absence of separating and sweating | 1 | 2 | 3 | 1 |
| | | Shape retention property | Moderate hardness | 2 | 2 | 4 | 2 |
| | | Appearance | Transparency | 5 | 1 | 3 | 1 |
| | | Ease of preparation | Ease of dissolution, ease of use | 5 | 1 | 1 | 3 |

As shown in Tables 19 and 20, it can be seen that the transparent lipsticks containing the cosmetic according to Examples 1-2 to 4-2 blended with an amino acid oil gelling agent, a polyamide resin and a specific monoester have as well as excellent usability such as ease of coating, sense of non-tackiness, adhesive property, and sufficient storage stability, and also have excellent appearance (high transparency) and high shape retention property.

To the contrary, it can be seen that Comparative examples 1-2 and 4-2 that do not contain an amino acid oil gelling agent, Comparative example 2-2 that does not contain a polyamide resin, and Comparative example 3-2 that does not contain a specific monoester were inferior in usability such as ease of coating, sense of non-tackiness, and adhesive feeling, storage stability, shape retention property and appearance (transparency) to Examples 1-2 to 4-2, and in particular storage stability is extremely low and shape retention property is largely inferior.

[Industrial Applicability]

According to the cosmetic of the present invention, as compared to conventional cosmetic, the one having two effects of excellent usability and sufficient storage stability in combination is provided. Therefore, the cosmetic of the present invention has particularly high industrial applicability in the wide field of cosmetic products such as a lip gloss, a lipstick, and a foundation, and greatly contributes to the development of cosmetic industry and related industries.

The invention claimed is:

1. A cosmetic comprising an amino acid oil gelling agent, a polyamide resin and a monoester, wherein the amino acid oil gelling agent is one or more comprising at least dibutyl lauroyl glutamide, and wherein said monoester is one or more selected from a monoester having a $C_9$ to $C_{24}$ linear chain or branched chain fatty acid moiety and/or a $C_9$ to $C_{24}$ linear chain or branched chain alcohol moiety, and said monoester is 20-80 mass % of the cosmetic;

wherein the monoester is one or more selected from the group consisting of isononanoate ester, 2-ethylhexanoate ester, myristate ester, isostearate ester, lactate ester, hydroxystearate ester, oleate ester, neopentanoate ester, palmitate ester, laurate ester, stearate ester, neodecanoate ester and nonanoate ester;

wherein the one or more amino acid oil gelling agent is 0.1 to 5 mass % of the cosmetic and the polyamide resin is 1.0 to 65 mass % of the cosmetic; and wherein the polyamide resin comprises an amide-terminated polyamide resin represented by the following general formula (2)

[Chem. 2]

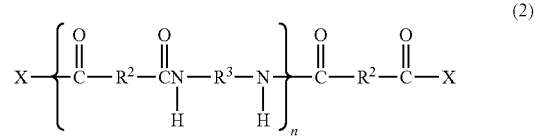

(2)

(wherein, X represents —N(R$^1$)$_2$ group, wherein R$^1$ represents a $C_8$ to $C_{22}$ linear chain or branched chain alkyl group which may be the same or different from each other, R$^2$ represents a dimer acid residue, R$^3$ represents an ethylenediamine residue, n represents an integer from 2 to 4).

2. A cosmetic product comprising the cosmetic according to claim 1.

3. The cosmetic product according to claim 2, selected from the group consisting of an antiperspirant, a cream, a lip gloss, an eye shadow, a mascara, a lip stick, a hair gel, a hair wax, a hair stick, a hair cream, a sun protection product, a foundation and an eye color.

4. A method for making the cosmetic according to claim 1, comprising dissolving the amino acid oil gelling agent, the polyamide resin, and the monoester to make a mixture.

5. A method for preparing a cosmetic, wherein the method comprises mixing one or more amino acid oil gelling agents, one or more polyamide resins, and one or more monoesters selected from the monoesters having a $C_9$ to $C_{24}$ linear chain or branched chain fatty acid moiety and/or a $C_9$ to $C_{24}$ linear chain or branched chain alcohol moiety, the one or more monoesters being 20-80 mass % of the cosmetic;

wherein the one or more amino acid oil gelling agents consist of dibutyl lauroyl glutamide;

wherein the monoester is one or more selected from the group consisting of isononanoate ester, 2-ethylhexanoate ester, myristate ester, isostearate ester, lactate ester, hydroxystearate ester, oleate ester, neopentanoate ester, palmitate ester, laurate ester, stearate ester, neodecanoate ester and nonanoate ester;

wherein the one or more amino acid oil gelling agent is 0.1 to 5 mass % of the cosmetic and the polyamide resin is 1.0 to 65 mass % of the cosmetic; and wherein the polyamide resin comprises an amide-terminated polyamide resin represented by the following general formula (2)

[Chem. 2]

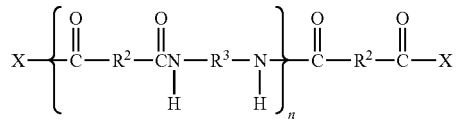

(wherein, X represents —N($R^1$)$_2$ group, wherein $R^1$ represents a $C_8$ to $C_{22}$ linear chain or branched chain alkyl group which may be the same or different from each other, $R^2$ represents a dimer acid residue, $R^3$ represents an ethylenediamine residue, n represents an integer from 2 to 4).

6. The cosmetic according to claim 1
wherein the amino acid gelling agent, the polyamide resin and the monoester together produce usability and storage stability.

7. The method according to claim 5
wherein the one or more amino acid gelling agents, the one or more polyamide resins and the one or more monoesters together produce usability and storage stability.

* * * * *